United States Patent [19]

Ueno et al.

[11] Patent Number: 5,212,200
[45] Date of Patent: May 18, 1993

[54] OCULAR HYPOTENSIVE AGENTS

[75] Inventors: Ryuzo Ueno; Ryuiji Ueno, both of Nishinomiya, Japan

[73] Assignee: R-Tech Ueno, Ltd., Osaka, Japan

[21] Appl. No.: 760,280

[22] Filed: Sep. 16, 1991

Related U.S. Application Data

[60] Division of Ser. No. 584,669, Sep. 19, 1990, Pat. No. 5,151,444, which is a continuation of Ser. No. 246,059, Sep. 19, 1988, Pat. No. 5,001,153.

[30] Foreign Application Priority Data

Sep. 18, 1987 [JP] Japan .................. 62-235890
Dec. 29, 1987 [JP] Japan .................. 62-334037

[51] Int. Cl.$^5$ ......................................... A61K 31/557
[52] U.S. Cl. ..................................... 514/530; 514/573
[58] Field of Search .............................. 514/530, 573

[56] References Cited

U.S. PATENT DOCUMENTS 5,073,569 12/1991 Ueno .................. 514/530

FOREIGN PATENT DOCUMENTS 0093380 11/1983 European Pat. Off. .
0242580 10/1987 European Pat. Off. .
0330511 8/1989 European Pat. Off. .
0364417 4/1990 European Pat. Off. .
1418 4/1984 Japan .
66122 2/1988 Japan .
107927 2/1988 Japan .

OTHER PUBLICATIONS

The Journal of Chromatography, vol. 156, 1978, pp. 131-141.
Arch. Int. Pharmacodyn., vol. 207, 1974, pp. 1310138.
Invest, Ophthalmol. Visual Sci., vol. 16, No. 12, Dec. 1977, pp. 1125-1134.
Acta Physiol. Scand., vol. 66, 1966, pp. 509-510.
Exp. Eye. Research 44, 825-837 (1987).
Graef's Arch. Clin. Exp. Ophthalmol. (1985) 222:139-141.
Investigative Ophthalmology and Visual Science by Bito, May 1982, vol. 22, No. 5.

*Primary Examiner*—Robert Gerstl
*Attorney, Agent, or Firm*—Sughrue, Mion, Zinn, Macpeak & Seas

[57] ABSTRACT

The present invention relates to ocular hypotensive agents which contains 13,14-dihydro-15-keto-prostagrandins, which shows no transient ocular hypertensive response that PGs usually show.

26 Claims, 1 Drawing Sheet

OCULAR HYPOTENSIVE AGENTS

This is a divisional of application Ser. No. 07/584,669 filed Sep. 19, 1990, now U.S. Pat. No. 5,151,494, in turn a continuation of application Ser. No. 07/246,059 filed Sep. 19, 1988, now U.S. Pat. No. 5,001,153.

BACKGROUND OF THE INVENTION

The present invention relates to ocular hypotensive agents which contains 13,14-dihydro-15-keto-prostaglandins.

Prosaglandins (hereinafter referred to as PGs) is the name given to the group of fatty acids which show various physiological activities and contained in human and animal tissues and organs. PGs essentially contain the prostanoic acid skeleton of the following formula:

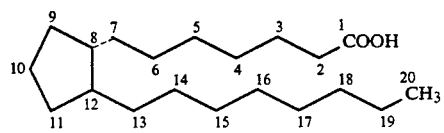

and some synthetic products may contain the above skeleton with some modification.

PGs are classified into several types according to their five-membered ring, for example,

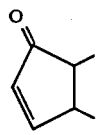

prostaglandins of the A series (PGAs):

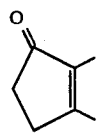

Prostaglandins of the B series (PGBs):

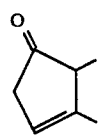

Prostaglandins of the C series (PGCs):

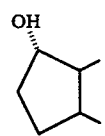

Prostaglandins of the D series (PDGs):

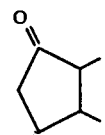

Prostaglandins of the E series (PGEs):

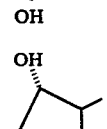

Prostaglandins of the F series (PGFS):

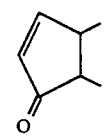

Prostaglandins of the J series (PGJs):

and the like. Further, they are classified into $PG_1s$ containing 5,6-single bond:

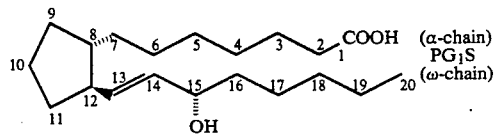

$PG_2s$ containing 5,6-double bond:

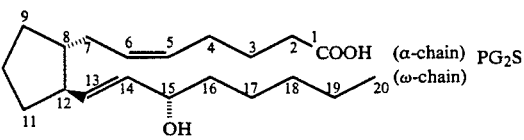

and $PG_3s$ containing 5,6-and 17,18-double bonds:

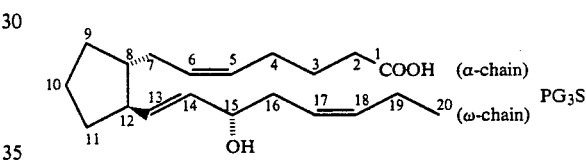

PGs are known to have various pharmacological and physiological activities, for example, vasodilation, induction of inflammation, platelet aggregation contraction of uterine muscle, enteron contraction and the like. However, PGs also possesses various other activities, therefore there are some problems to use them as medicines. That is, when PGs are administered to obtain a single pharmaceutical activity, they often exhibit other activities as side effects. Accordingly, the investigations of PGs as a medicine have aimed to enhance the emergency of the main pharmaceutical activity. However, these investigations have been insufficient Among PGs, for example, PGAs, PGDs, PGEs, PGFs are known to possess ocular hypotensive potency.

For example, there is described in Japanese Patent Application KOKAI No. 1418/1984 claiming a priority based on U.S. Ser. No. 374,165(1982) by Laszlo Z. Bite that $PGF_2$ has a high ocular hypotensive activity, and 15-keto-$PGF_2\alpha$ has also it though a very little; and further in Japanese Patent Application KOKAI No. 66122/1988 claiming priorities based on three U.S. Ser. Nos. 839,056 (1986), 892,387(1986) and 022,046 (1987) that PGA, PGB and PGC can be used for a treatment of glaucoma However, when topical application of these PGs, topically to rabbit eyes, they are accompanied with transient ocular hypertensive response, and still pronounced conjunctival and iridal hyperemia, and further side effects such as lacrimation, eye mucus, lid closure and the like are observed. Accordingly, there are some problems when PGs are used as remedies for glaucoma or ocular hypotensive agents On the other hand, PGs wherein the carbon atoms at the 13-14 positions are saturated and the carbon atom at the 15 position forms a carbonyl group are found to exist in human or animal metabolites. These 13,14-dihydro-15-ketoprostaglandins (hereinafter referred to as 13,14-dihydro-15-keto-PGs) are known to be naturally produced metabolites by enzymatic metabolism of the corresponding PGs in vivo. These 13,14-dihydro-15-keto-PGs have been reported to hardly exhibit various physiological activities that PGs possess and be pharmacologically and physiologically inactive metabolites (see, Acta Physiologica Scandinavica, 66, p.509-(1966))

SUMMARY OF THE INVENTION

It has been found the above metabolites cause intraocular pressure reduction without any transient ocular hypertensive response that PGs usually show. Further, among 13,14-dihydro-15-keto-PGs, or carboxylic acid, salts, esters, compounds having a 2,3-double bond, or a 5,6-triple bond, or compounds having substituents at any of C-3, C-6, C-16, C-17, C-19 and/or C-20 positions, compounds having a lower alkyl or hydroxyalkyl group at the C-9 and/or C-11 position instead of the hydroxyl group, posses enhanced ocular hypotensive potency, and these 13,14-dihydro-15-keto-PGs may exhibit ocular hypotensive effect without transient ocular hypertensive response, and with absolutely no or extremely reduced side effects such as hyperemia. Further, we have found that these 13,14-dihydro-15-keto-PGs are accompanied with no or extremely reduced peculiar central and peripheral physiological activities which are simultaneously caused by PGs, and further they have no effects on enteron, trachea or bronchus which are characteristic of PGs.

DETAILED DESCRIPTION OF THE INVENTION

Figure 1:
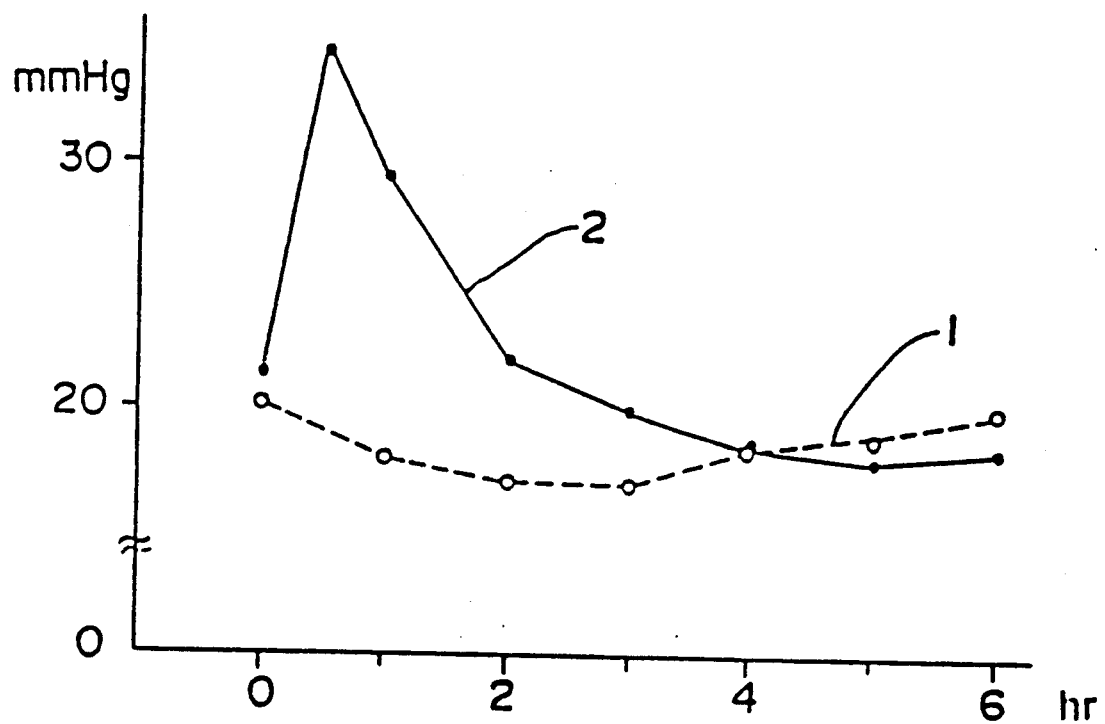
FIG. 1 is a graph showing change in intraocular pressure with time after application of prostaglandins $E_2$ to rabbits, wherein applied drugs were as follows: (1):13,14-dihydro-15-keto-$PGE_2$ (2):$PGE_2$

The present invention provides ocular hypotensive agents containing 13,14-dihydro-15-keto-PGs as active ingredients.

In the present invention, 13,14-dihydro-15-keto-PGs means PGs wherein carbons at the 13-14 positions are saturated and carbon at the 15 position forms a carbonyl group.

In this description, 13,14-dihydro-15-keto-PGs are expressed as follows. That is, in 13,14-dihydro-15-keto-PGs, the carbons constituting the α-chain, ω-chain and 5-membered ring are numbered according to the basic skeleton as follows:

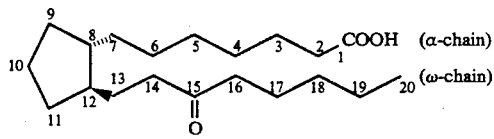

That is, in the basic skeleton, the constituent carbon atoms are numbered in such a way that the carbon atom in carboxylic acid is C-1, and the α-chain contains C-2 - C-7, the number increasing toward the ring, the five-membered ring contains C-8 - C-12, and the ω-chain contains C-13 - C-20. When the carbons of the α-chain are fewer, the n of the carbons ensuing C-2 should be properly shifted, and when more than 7, the compound is named provided that the carbon at the 2 position has a substituent instead of the carboxyl group (at C-1 position). When the ω-chain contains fewer carbon atoms, they should be numbered correspondingly smaller than 20, and when more than 8, the carbon atoms at the 21 position and thereafter should be regarded as a substituent. As configuration, it is considered according to that of the above essential skeleton unless otherwise described.

For example, PGD, PGE and PGF mean compounds having a hydroxyl group at the C-9 and/or C-11 positions. In the present intention, PGs include those having other group instead of the hydroxyl group o the C-9 and/or C-11 positions, they being named as 9-dehydroxy-9-substituted or 11-dehydroxy-11-substituted compounds.

13,14-Dihydro-15-keto-PGs used in the present invention may be PGs wherein the carbon atoms at the 13-14 positions are saturated and the carbon atom at the 15 position forms a carbonyl group, and 13,14-dihydro-15-keto-$PG_1$s containing a 5,6-single bond, 13,14-dihydro-15-keto-$PG_2$s containing a 5,6-double bond, 13,14-dihydro-15-keto-$PG_3$s containing both 5,6- and 17,18-double bonds may be used.

The typical examples of the 13,14-dihydro-15-keto-PGs used in the present invention are shown below:

13,14-dihydro-15-keto-$PGA_1$s, 13,14-dihydro-15-keto-$PGA_2$s,
13,14-dihydro-15-keto-$PGA_3$s, 13,14-dihydro-15-keto-$PGB_1$s,
13,14-dihydro-15-keto-$PGB_2$s, 13,14-dihydro-15-keto-$PGB_3$s,
13,14-dihydro-15-keto-$PGC_1$s, 13,14-dihydro-15-keto-$PGC_2$s,
13,14-dihydro-15-keto-$PGC_3$s, 13,14-dihydro-15-keto-$PGD_1$s,
13,14-dihydro-15-keto-$PGD_2$s, 13,14-dihydro-15-keto-$PGD_3$s,
13,14-dihydro-15-keto-$PGE_1$s, 13,14-dihydro-15-keto-$PGE_2$s,
13,14-dihydro-15-keto-$PGE_3$s, 13,14-dihydro-15-keto-$PGF_1$s,
13,14-dihydro-15-keto-$PGF_2$s, 13,14-dihydro-15-keto-$PGF_3$s,
13,14-dihydro-15-keto-$PGJ_1$s, 13,14-dihydro-15-keto-$PGJ_2$s,
13,14-dihydro-15-keto-$PGJ_3$s or the like.

These 13,14-dihydro-15-keto-PGs show strong ocular hypotensive potency without showing transient ocular hypertensive response as well as side effects such as pronounced conjunctival or iridal hyperemia, lacrimation, lid closure and the like, or extremely reduced, if any. Accordingly, these 13,14-dihydro-15-keto-PGs are extremely effective as ocular hypotensive agents. Further depending on such ocular hypotensive effect, they may be used for glaucoma therapy.

In the present invention, the ocular hypotensive effect of 13,14-dihydro-15-keto-PGs may be especially remarkable in prostaglandins of the general formula:

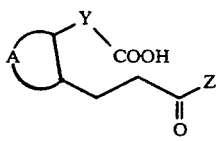

[I]

[wherein, A is

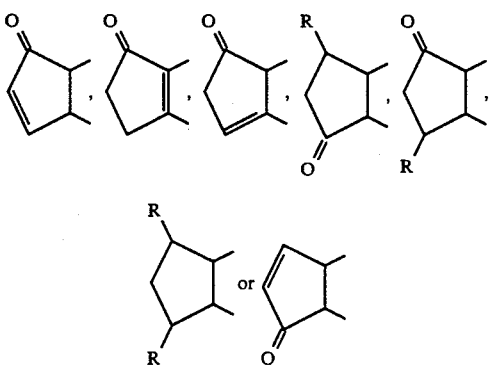

which R is hydroxyl, hydroxyalkyl or alkyl); Y is a saturated or unsaturated $C_{2-6}$ hydrocarbon chain (some of the carbon atoms constituting the hydrocarbon chain may form a carbonyl group, and the hydrocarbon chain may be substituted with one or more atoms or groups); Z is a $C_{1-10}$ saturated or unsaturated hydrocarbon forming a straight-chain, branched-chain or ring (the hydrocarbon may be substituted with atoms or groups)] or physiologically acceptable salts derived from the general formula [I] or those having an esterified carboxyl group.

A saturated or unsaturated $C_{2-6}$ hydrocarbon chain Y includes a straight hydrocarbon chain such as an alkyl, alkenyl, alkynyl and the like. Especially, a hydrocarbon chain with 6 carbons is preferred.

The examples of an unsaturated hydrocarbon chain Y include, for example, PGs wherein carbons at 2-3 positions or 5-6 positions are unsaturatedly bonded.

Some of the carbons forming the hydrocarbon chain Y may form a carbonyl group. The typical example includes 6-keto-PG₁s wherein the carbon at the 6 position constituting a carbonyl group.

The hydrocarbon chain Y may be substituted with one or more atoms or groups. Such atoms or groups include, for example, a halogen atom such as a fluorine, chlorine or bromine atom; an alkyl group such as methyl, ethyl; a hydroxyl group. The typical example is PGs having one or more alkyl groups at the carbon at the 3 position.

Z means a $C_{1-10}$ saturated or unsaturated hydrocarbon group. The hydrocarbon itself may form a ring or may be substituted with one or more atoms or groups.

As the hydrocarbon group Z, those with a $C_{3-9}$ straight chain are particularly preferred. Those with five carbons corresponds to the general PGs with an ω-chain having eight carbons. Accordingly, as described above, the hydrocarbon Z having more than 6 carbons are assumed to be a substituent of the carbon at the 20 position in the ω-chain (i.e., a hydrocarbon having seven carbons may be referred to as 20-ethyl-PGs).

The unsaturated bond may be at any position in Z. However, Z without an unsaturated bond is preferred. The examples of the hydrocarbon Z forming a ring include a cyclo-pentyl or cyclohexyl group wherein carbons at 16 or 17 position in the ω-chain may be constituent of the ring.

The hydrocarbon Z may be substituted with one or more atoms or groups. Such atoms or groups include a halogen atom such as a fluorine, chlorine or bromine atom; an alkyl group such as a methyl, ethyl, isopropyl or isopropenyl group; an alkoxy group such as a methoxy or ethoxy group; a hydroxyl group; a phenyl group; a phenoxy group and the like. The position of the substituent atom(s) or group(s) may not be limited, but typically, they may be at 16, 17, 19 and/or 20 position in the ω-chain. Particularly, compounds having one or two same or different atoms at the C-16 position, for example, a halogen atom such as a fluorine atom or a substituent, for example, an alkyl group such as a methyl, ethyl, hydroxyl phenyl which may contain one or more substituents, benzyl, phenoxy, or cycloalkyl group such as a cyclopentyl or cyclohexyl group which contains the C-16 position as a constituent; an alkyl group such as methyl at the C-17 or C-19 position: an alkyl group such as a methyl, ethyl, isopropyl, isopropenyl or alkoxy group such as a methoxy, ethoxy or propoxy group at the C-20 position are preferred.

PGs may include the compounds PGD, PGE, PGF which contain a hydroxyl group at the C-9 and/or C-11 position. In the present invention, PGs further include the compounds having a hydroxyalkyl or alkyl group instead of the hydroxyl group at the C-9 and/or C-11 position. Accordingly, the 13,14-dihydro-15-keto-PGs of the present invention include the compound of the general formula [I], wherein R is a hydroxyl, hydroxyalkyl or alkyl group. Such hydroxyalkyl group preferably include a hydroxymethyl or 1-hydroxyethyl, 2-hydroxyethyl or 1-methyl-1-hydroxyethyl group. As the alkyl group, a lower alkyl group, especially a methyl or ethyl group are preferred.

The configuration of R for the carbon at the 9 and/or 11 position may be an α, β or mixture thereof.

PGs of the present invention may be salts or those with an esterified carboxyl group. Such salts include physiologically acceptable salts, for example, those of an alkali metal such as sodium, potassium; those of an alkaline earth metal such as calcium, magnesium; those of physiologically acceptable an ammonium salt such as ammonia, methylamine, dimethylamine, cyclopentylamine, benzylamine, piperidine, monoethanolamine, diethanolamine, monomethylmonoethanolamine, tromethamine, lysine, tetralkylammonium salt and the like. Such an ester includes, for a example, methyl, ethyl, propyl, butyl, isopropyl, t-butyl, 2-ethylhexyl, straight or branched-chain alkyl ester which may contain an unsaturated bond; for example, ester having an alicyclic group such as a cyclopropyl, cyclopentyl or cyclohexyl group: an ester containing an aromatic group such as a benzyl or phenyl group (wherein the aromatic group may contain one or more substituents); a hydroxyalkyl or alkoxyalkyl ester such as a hydroxyethyl, hydroxyisopropyl, polyhydroxyisopropyl. methoxyethyl, ethoxyethyl or methoxyisopropyl group; an alkylsilyl ester e.g., a trimethylsilyl or triethylsilyl ester: a tetrahydropyranyl ester.

Preferred esters include, for example, a straight or branched lower alkyl ester such as a methyl, ethyl, propyl, n-butyl, isopropyl or t-butyl ester; or a benzyl ester; a hydroxyalkyl ester such as a hydroxyethyl or hydroxyisopropyl ester.

The carboxyl group at the C-1 position of 13,14-dihydro-15-keto-PGs of the present invention may be any of the above described groups. Among them, esters, especially the $C_{1-4}$ alkyl ester are preferred considering emergency of ocular hypotensive effect.

13,14-Dihydro-15-keto-PGs of the present invention may include the isomers of the above compounds. Examples of such isomers include keto-hemiacetal tautomers between the $C_6$-carbonyl and $C_9$-hydroxyl, or the $C_{11}$-hydroxyl and $C_{15}$-carbonyl; or optical isomers; geometrical isomers and the like.

Keto-hemiacetal tautomers between the $C_{11}$-hydroxyl group and $C_{15}$-carbonyl may be readily formed especially in 13,14-dihydro-15-keto-PGEs having electrophilic group such as a fluorine atom at the C-16 position.

The mixture of the isomers, for example, those of racemic body, tautomers of hydroxyl compound and hemiacetals may show similar effect as that shown by the respective compound.

In the present invention, especially preferred 13,14-dihydro-15-keto-PGs may contain a 5,6-single or double bond, or a carbonyl group at the 6 position carbon atom. Another preferred groups are 13,14-dihydro-15-keto-PGs having 20 - 24 carbon atoms. Still other preferred groups are 13,14-dihydro-15-keto-PGs wherein the carbon atom at the 16 position may be substituted with a halogen atom or an alkyl group, and further, 13-14-dihydro-15-keto-PGs having more than 20 carbons and an alkyl group at C-19 position.

Particularly, the compounds having a $C_{1-4}$ alkyl, for example, a methyl, ethyl, propyl or butyl group at the C-20 position, that is, having a prolonged ω-chain show enhanced ocular hypotensive effect with little side effects such as hyperemia. Accordingly, such compounds are preferred.

That is, in 13,14-dihydro-15-keto-PGs used in the present invention, those having an alkyl group at the C-20 position may provide particularly preferable result, neglecting the structure of the five-membered ring, or the existence of double bond or other substituents. Particularly, those wherein the alkyl group is ethyl (wherein the ω-chain contains a $C_{10}$ straight chain) may show the most pronounced ocular hypotensive effect, scarcely showing side effects such as hyperemia, thereby providing the most preferable product as a whole.

In the present invention, PGs are named according to the prostanoic acid skeleton. If named according to IUPAC, for example, $PGE_1$ corresponds to 7-[(1R,2R,3R)-3-hydroxy-2-(E)-(3S)-3-hydroxy-1-octenyl]-5-oxo-cyclopentyl]-heptanoic acid; $PGE_2$, (Z)-7-[(1R,2R,3R)-3-hydroxy-2-[(E)-(3S)-3-hydroxy-1-octenyl]-5-oxo-cyclopentyl]-hept-5-enoic acid; 13,14-dihydro-15-keto-16R,S-fluoro-$PGE_2$, (Z)-7-[(1R,2S,3R)-2-[(4RS)-4-fluoro-3-oxo-1-octyl]-3-hydroxy-5-oxo-cyclopentyl]-hept-5-enoic acid; 13,14-dihydro-15-keto-20-ethyl-11-dehydroxy-11R-methyl-$PGE_2$ methyl ester, methyl 7-[(1R,2S,3R)-3-methyl-2-(3-oxo-1-decyl)-5-oxo-cyclopentyl]-hept-5-enoate; 13,14-dihydro-6,15-diketo-19-methyl-$PGE_2$ ethyl ester, ethyl 7-[(1R,2R,3R)-3-hydroxy-2-(7-methyl-3-oxo-1-octyl)-5-oxo-cyclopentyl]-6-oxo-heptanoate. $PGF_{1\alpha}$ corresponds to 7-[(1R,2R,3R,5S)-3,5-dihydroxy-2-[(E)-(3S)-3-hydroxy-1-octenyl]-cyclopentyl]-5-heptenoic acid; $PGF_{2\alpha}$, (Z)-7-[(1R,2R,3R,5S)-3,5-dihydrocy-2-[(D)-(3S)-3-hydroxy-1-octenyl]-cyclopentyl]-5-heptenoic acid; 13,14-dihydro-15-keto-20-ethyl-$PGF_{2\alpha}$ isopropyl ester, isopropyl (Z)-7-[(1R,2R,3R,5S)-3,5-dihydroxy-2-(3-oxo-1-decyl)-cyclopentyl]-hept-5-enoate; 13,14-dihydro-15-keto-20-methyl-$PGF_{2\alpha}$ methyl ester, methyl (Z)-7-[(1R,2R,3R,5S)-3,5-dihydroxy-2-(3-oxo-1-nonyl)-cyclopentyl]-hept-5-enoate. Other PGs may also be named in the same way.

13,14-Dihydro-15-keto-PGs of the present invention include isomers of the above compounds. The example of these isomers includes keto-hemiacetal tautomers between the C-6 carbonyl and C-9 hydroxyl groups, or the C-11 hydroxyl and C-15 carbonyl groups; or optical isomers; geometrical isomers and the like.

The keto-hemiacetal tautomers between the C-11 hydroxyl and C-15 carbonyl groups may be readily formed, for example, in the case of 13,14-dihydro-15-keto-PGs which contain one or more electrophilic groups such as a fluorine atom at the 16 position. The mixture of the isomers, for example, those of racemic body or tautomers of the hydroxy compound with hemiacetals may shown similar effect as that shown by a respective compound.

The above 13,14-dihydro-15-keto-PGs of the present invention may be prepared according to the methods described, for example, in Japanese Patent Application Nos. 63-18326, 63-18327 and 63-108329. These descriptions may be included in the present invention.

In the process for preparing 13,14-dihydro-15-keto-compound: A commercially available (-)-Corey lactone, which is used as a starting material, is subjected to Collins oxidation to give an aldehyde. The aldehyde is allowed to react with dimethyl (2-oxoalkyl)phosphonate anion to give an α,β-unsaturated ketone and the resultant is reduced to ketone. The carbonyl group of the ketone is allowed to react with a diol to give a ketal, thereby protected, then a corresponding alcohol is obtained by elimination of the phenylbenzoyl group, and the resulting hydroxy group is protected with dihydropyran to give a tetrapyranyl ether. Thus, precursors of PGs wherein the ω-chain is 13,14-dihydro-15-keto-alkyl can be obtained.

Using the above tetrapyranyl ether as a starting material, 6-keto-$PG_1$s of the formula:

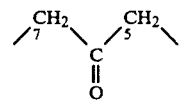

may be obtained as follows:

The tetrapyranyl ether is reduced using diisobutyl aluminium hydride and the like to give a lactol, which is allowed to react with a ylide obtained from (4-carboxybutyl)triphenylphosphonium bromide, and the resultant is subjected to esterification followed by cyclization, combining the 5,6-double bond and the C-9 hydroxyl group with NBS or iodine, providing a halide. The resultant is subjected to dehydrohalogenation with DBU and the like to give a 6-keto compound, which is subjected to Jones oxidation followed by deprotection to give the objective compound.

Further, $PG_2$s of the formula:

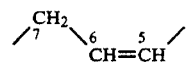

may be obtained as follows:

The above tetrapyranyl ether is reduced to the lactol, which is allowed to react with a ylide obtained from (4-carboxybutyl)triphenylphosphonium bromide to give a carboxylic acid. The resultant is subjected to esterification followed by Jones oxidation and deprotection to give the objective compound.

In order to obtain PG$_1$s of the formula:

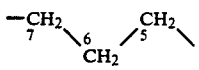

using the above tetrapyranyl ether as a starting material, in the same manner as PG$_2$ of the formula:

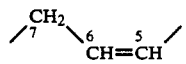

the 5,6-double bond of the resulting compound is subjected to catalytic reduction followed by deprotection. To prepare 5,6-dehydro-PG$_2$s containing a hydrocarbon chain of the formula:

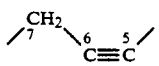

a monoalkyl copper complex or a dialkyl copper complex of the formula:

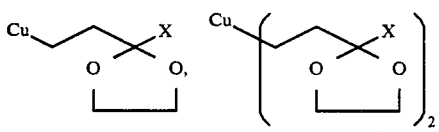

is subjected to 1,4-addition with 4R-t-butyldimethylsilyloxy-2-cyclopenten-1-one, and the resulting copper enolate is seized with 6-carboalkoxy-1-iodo-2-hexyne or a derivative thereof.

PGs containing a methyl group instead of a hydroxy group at the C-11 position may be obtained as follows: PGA obtained by Jones oxidation of the hydroxy group at the C-9 position of the 11-tosylate is allowed to react with a dimethyl copper complex to give 11-dehydroxy-11-methyl-PGE. Alternatively, an alcohol obtained after elimination of p-phenylbenzoyl group is converted to a tosylate. An unsaturated lactone obtained by DBU treatment of the tosylate is converted to a lactol. After introduction of an α-chain using Wittig reaction, the resulting alcohol (C-9 position) is oxidized to give PGA. PGA is allowed to react with dimethyl copper complex to give 11-dehydroxy-11-methyl-PGE. The resultant is reduced using sodium borohydride and the like to give 11-dehydroxy-11-methyl-PGF.

PGs containing a hydroxymethyl group instead of a hydroxyl group at the C-11 position is obtained as follow: 11-dehydroxy-11-hydroxymethyl-PGE is obtained by a benzophenone-sensitized photoaddition of methanol to PGA. The resultant is, for example, reduced using sodium borohydride to give 11-dehydroxy-11-hydroxymethyl-PGF 16-Fluoro-PGs may be obtained using dimethyl (3-fluoro-2-oxoalkyl)phosphonate anion in the preparation of an α,β-unsaturated ketone. Similarly, 19-methyl-PGs may be obtained using a dimethyl (6-methyl-2-oxoalkyl)phosphonate anion.

The preparations in the present invention are not construed to be limited to them, and suitable means for protection, oxidation, reduction and the like may be employed.

13,14-Dihydro-15-keto-PGs of the present invention can be used as remedies for animal and human, and, in general, used for systemic or local application by oral administration, intravenous injection, subcutaneous injection, suppository, collyrium, oculentum and the like. The dosage varies depending on animals, human, age, weight, conditions, therapeutic effect, administration route, treatment time and the like.

The solid composition for oral administration of the present invention includes tablets, preparations, granules and the like. In such a solid composition, one or more active ingredients may be mixed with at least one inactive diluent, for example, lactose, mannitol, glucose, hydroxypropyl cellulose, microcrystalline cellulose, starch, polyvinyl pyrrolidone, magnesium aluminate metasilicate and the like. According to the usual work-up, the composition may contain additives other than an inactive diluent, for example, a lubricant such as magnesium stearate; disintegrant such as fibrous calcium gluconate; a stabilizer such as etherified cyclodextrin, for example, α,β- or γ-cyclodextrin, dimethyl-α-, dimethyl-β-, trimethyl-β- or hydroxypropyl-β-cyclodextrin, branched cyclodextrin such as glucosyl-, maltosyl-cyclodextrin, formylated cyclodextrin, cyclodextrin containing sulfur, mitthoprotol, phospholipid and the like. When the above cyclodextrins are used, an inclusion compound with cyclodextrins may be sometimes formed to enhance stability. Alternatively, a phospholipid may be sometimes used to form a liposome, resulting in enhanced stability.

Tablets or pills may be coated with film soluble materials in the stomach or intestine such as sugar, gelatin, hydroxypropyl cellulose, hydroxypropylmethyl cellulose phthalate and the like, or with more than two layers. Further, they may be formed as capsules with absorbable substances such as gelatin.

A liquid composition for oral administration may contain a pharmaceutically acceptable emulsion, solution, suspension, syrup, elixir as well as a generally used inactive diluent, for example, purified water, ethanol and the like. Such a composition may contain, in addition to the inactive diluent, adjuvants such as wetting agents and suspensions, sweetening agents, flavoring agents, preservatives and the like.

Other compositions for oral administration include a spray formulated by known method, which may contain one or more active ingredients.

Injection for parenteral administration according to the present invention includes a steril, agueous or nonaqueous solution, suspension, emulsion and the like.

A diluent for such an aqueous solution and suspension includes, for example, injectable distilled water, physiological saline and Ringer's solution.

A diluent for non-aqueous solution and suspension includes, for example, propylene glycol, polyethylene glycol, vegetable oil such as olive oil, alcohols such as ethanol, polysorbate and the like. Such a composition may contain adjuvants such as preservatives, wetting agents, emulsifiers, dispersants, stabilizers and the like. These are sterilized, for example, by filtration through a bacteria-holding filter, compounding with germicides, gas sterilization or radio-sterilization. These may be used by preparing a sterile solid composition and dissolving in sterile water or sterile solvent for injection before use.

The collyrium according to the present invention may include a sterile aqueous or non-aqueous solution, suspension and the like. The diluent for such an aqueous solution or suspension includes, for example, distilled water or a physiological saline. The diluent for the non-aqueous solution or suspension may include an edible oil, liquid paraffin, mineral oil, propylene glycol, p-octyldodecanol and the like. Further, in order to make isotonic to tears, isotonic agents such as sodium chloride, benzalkonium chloride, phedrine chloride, procaine chloride, chloram phenicol, sodium citrate, or in order to maintain the pH value constant, buffer such as a borate or phosphate buffer may be used. Moreover, stabilizers such as sodium sulfite, sodium carbonate, EDTA, propylene glycol; thickening agents such as glycerin, carboxymethyl cellulose, carboxyvinyl polymer; diluents such as polysorbate, macrogols, alminum monostearate; preservatives such as paraben, benzyl alcohol, sorbic acid; and further resolvents, vehicles may be compounded. These may be sterilized, for example, by the filtration through a bacteria-holding filter or heat sterilization. In the preparation of collyrium, pH value and ion strength of the agent are especially important, and they may be optionally adjusted to the optimal value depending on the types and amounts of other active ingredients or additives used.

The oculentum according to the present invention may contain vaseline, selen 50, plastibase, macrogols as a base, and surfactant such as polysorbate, Tween, purified lanolin, jelly such as carboxymethyl cellulose, methylcellulose, carboxyvinyl polymer to enhance hydrophilism.

The ocular hypotensive agent of the present invention may be used as a remedy for glaucoma utilizing its ocular hypotensive potency. When used as the remedie for treatment of glaucoma, the present agents may be compounded with the conventional cholinergic ocular hypotensive agent (e.g., pilocarpine, carbachol, which possesses excellent miotic activity) anticholinesterases (e.g., demecarium, D.F.P., echothiophate), physostigmine salicylate, pilocarpine hydrochloride as miotics, mannitol, glycerin, isosorbide as hyperosmotic agent for intravenous injection, chlorobutanol, benzalkonium chloride, propylparabene, methylparaben, ethylparaben, butylparaben as preservatives for collyrium, penicillin, sulfonamide, chloramphenicol, cortisone, chlorpheniramine for prevention and treatment of other inflammation.

The present invention will be illustrated in the following examples.

PREPARATIONS

Preparations of 13,14-dihydro-15-keto-20-ethyl-PGA$_2$ isopropyl ester, 13,14-dihydro-15-keto-20-ethyl-PGE$_2$ isopropyl ester and 13,14-dihydro-15-keto-20-ethyl-PGF$_{2\alpha}$ isopropyl ester (cf. Preparation chart I):

1) Preparation of 1S-2-oxa-3-oxo-6R-(3-oxo-1-transdecenyl)-7R-(4-phenylbenzoyloxy)-cis-bicyclo[3.3.0]-octane (3)

Commercially available (-)-Corey lactone (1) (7 g) was subjected to Collins oxidation in dichloromethane to give aldehyde (2). The resultant was allowed to react with dimethyl (2-oxononyl)phosphonate (4.97 g) anion to give 1S-2-oxa-3-oxo-6R-(3,3-ethylendioxy-1-transdecenyl)-7R-(4-phenylbenzoyloxy)-cis-bicyclo[3.3.0-octane (3).

2) Preparation of 1S-2-oxa-3-oxo-6R-(3-oxodecyl)-7R-(4-phenylbenzoyloxy)-cis-bicyclo[3.3.0]-octane (4)

Unsaturated ketone (3) (7 80 g was reduced in ethyl acetate (170 ml) using 5% Pd/C under hydrogen atmosphere. The product obtained after the usual work-up (4) was used in the following reaction.

3) Preparation of 1S-2-oxa-3-oxo-6R-(3,3-ethylenedioxy-decyl)-7R-(4-phenylbenzoyloxy)-cis-bicyclo[3.3.0]-octane (5)

Saturated ketone (4) was converted to ketal (5) in dry benzene (150 ml) using ethylene glycol and p-toluenesulfonic acid (catalytic amount).

4) Preparation of 1S-2-oxa-3-oxo-6R-(3,3-ethylenedioxy-decyl)-7R-hydroxy-cis-bicyclo[3.3.0]-octane (6)

To a solution of ketal (5) in absolute methanol (150 ml) was added potassium carbonate (2.73 g). The mixture was stirred overnight at room temperature. After neutralization with acetic acid, the resultant was concentrated under reduced pressure. The resulting crude product was extracted with ethyl acetate. The organic layer was washed with a dilute aqueous solution of sodium bicarbonate and a saline, and dried. The crude product obtained after evapolation was chromatographed to give alcohol (6). Yield; 3.31 g

5) Preparation of lactol (7)

Alcohol (6) (0.80 g) was reduced in dry toluene (8 ml) using DIBAL-H at -78 ° C to give lactol (7).

6) Preparation of 13,14-dihydro-15,15-ethylenedioxy-20-ethyl-PGF$_{2\alpha}$ (8)

A DMSO solution of lactol (7) was added to ylide prepared from (4-carboxybutyl)triphenylphosphonium bromide (3.65 g). The reaction mixture was stirred overnight to give carboxylic acid (8).

7) Preparation of 13,14-dihydro-15,15-ethylenedioxy-20-ethyl-PGF$_{2\alpha}$ isopropyl ester (9)

Carboxylic acid (8) was converted to 13,14-dihydro-15,15-ethylenedioxy-20-ethyl-PGF$_{2\alpha}$ isopropyl ester (9) using DBU and isopropyl iodide in acetonitrile.
Yield; 0.71 g

8) Preparation of 13,14-dihydro-15-keto-20-ethyl-PGF$_{2\alpha}$ isopropyl ester (10)

13,14-Dihydro-15,15-ethylenedioxy-20-ethyl-PGF$_{2\alpha}$ isopropyl ester (9) (0.71 g) was kept in acetic acid/THF/water (3/1/1) at 40 ° C. for 3 hours. The crude product obtained after concentration under reduced pressure was chromatographed to give 13,14-dihydro-15-keto-20-ethyl-PGF$_{2\alpha}$ isopropyl ester (10).
Yield; 0.554 g

9) Preparation of 13,14-dihydro-15-keto-20-ethyl-PGA$_2$ isopropyl ester (12)

A solution of 13,14-dihydro-15-keto-20-ethyl-PGF$_{2\alpha}$ isopropyl ester (10) (0.125 g) and p-toluenesulfonyl chloride (0.112 g) in pyridine (5 ml) was maintained at 0° C. for 2 days. According to the usual work-up, tosylate (11) was obtained.

Tosylate (11) was subjected to Jones oxidation in acetone (8 ml) at −25° C. The crude product obtained after the usual work-up was chromatographed to give 13,14-dihydro-15-keto-20-ethyl-PGA$_{2\alpha}$ isopropyl ester (2).

Yield; 0.060 g

10) Preparation of 13,14-dihydro-15,15-ethylenedioxy-20-ethyl-11-t-butyldimethylsiloxy-PGF$_{2\alpha}$ isopropyl ester (13)

13,14-Dihydro-15,15-ethylenedioxy-20-ethyl-PGF$_{2\alpha}$ isopropyl ester (9) (3.051 g) was dissolved in dry N,N-dimethylformamide (25 ml), t-butyldimethylsilyl chloride (1.088 g) and imidazole (0.49 g) was added thereto. The resultant was stirred at room temperature overnight. The reaction mixture was concentrated under reduced pressure, and the resulting crude product was chromatographed to give 13,14-dihydro-15,15-ethylenedioxy-20-ethyl-11-t-butyldimethylsiloxy-PGF$_{2\alpha}$ isopropyl ester (13).

Yield; 2.641 g

11) Preparation of 13,14-dihydro-15,15-ethylenedioxy-20-ethyl-11-t-butyldimethylsiloxy-PGE$_2$ isopropyl ester (14)

13,14-Dihydro-15,15-ethylenedioxy-20-ethyl-11-t-butyldimethylsiloxy-PGF$_{2\alpha}$ isopropyl ester (13) (1.257 g) was subjected to Jones oxidation at −40° C. After the usual work-up, the resulting crude product was chromatographed to give 13,14-dihydro-15,15-ethylenedioxy-20-ethyl-11-t-butyldimethylsiloxy-PGE$_2$ isopropyl ester (14).

Yield; 1.082 g

12) Preparation of 13,14-dihydro-15-keto-20-ethyl-PGE$_2$ isopropyl ester (15)

To a solution of 13,14-dihydro-15,15-ethylenedioxy-20-ethyl-11-t-butyldimethylsiloxy-PGE$_2$ isopropyl ester (14) in acetonitrile was added hydrofluoric acid (46% aqueous solution). The mixture was stirred at room temperature for 40 minutes. The crude products obtained after usual work-up was chromatographed to give 13,14-dihydro-15-keto-20-ethyl-PGE$_2$ isopropyl ester (15).

Yield; 0.063 g (97 %)

Preparation Chart

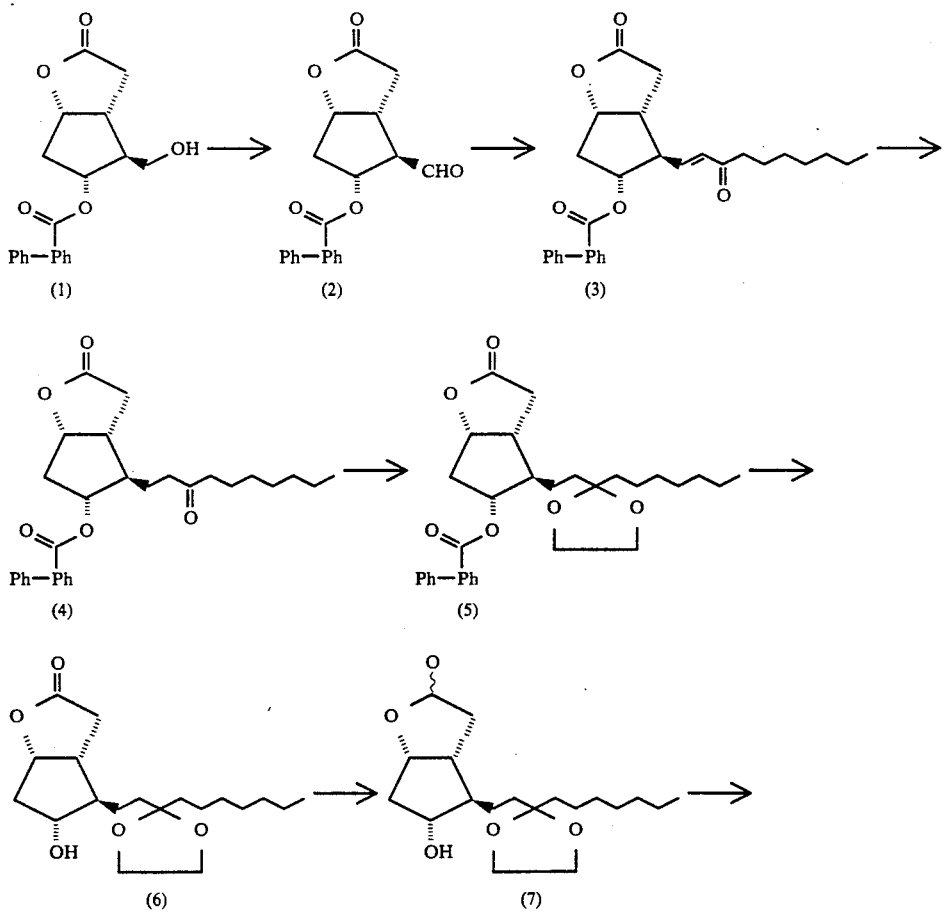

-continued
Preparation Chart

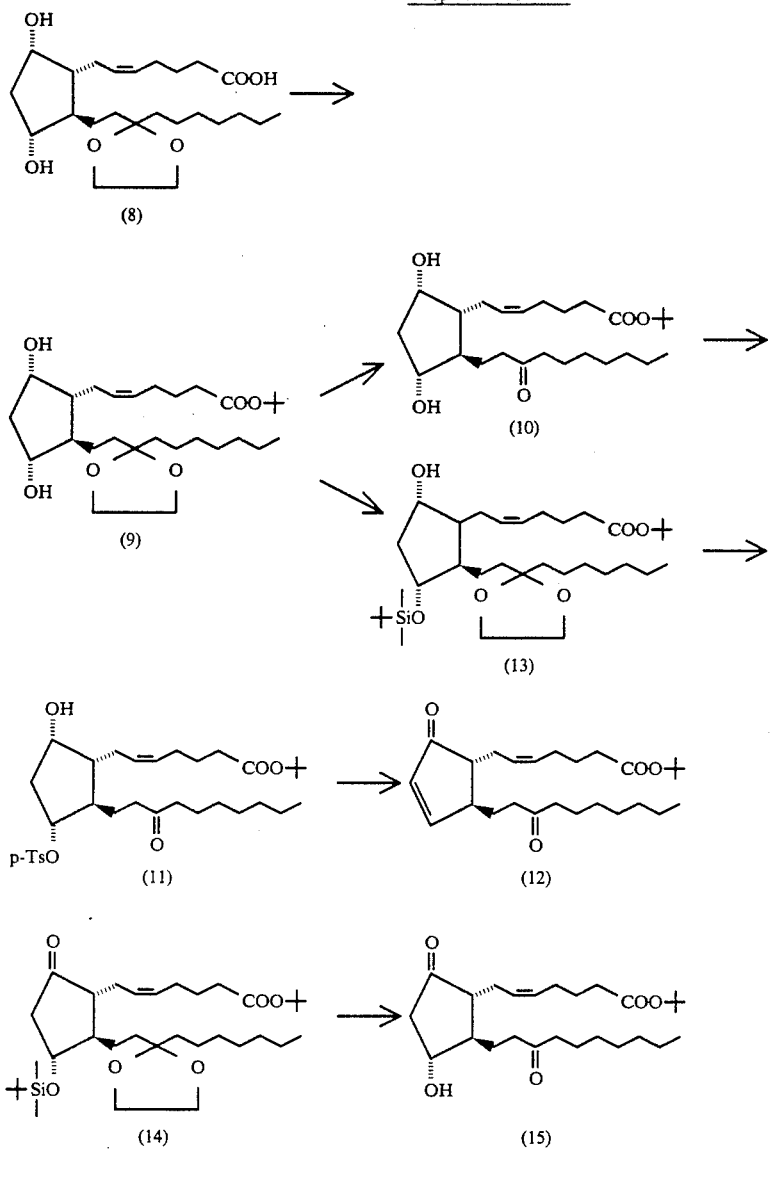

+: iso-propyl

EXAMPLE 1

For the purpose of tonometry, Japanese White male rabbits (2.5-3.0 Kg) were fixed on braces, and after topical anesthetization with 0.4% oxybuprocaine hydrochloride, intraocular pressure was measured using a pheumatic applanation tonometer (manufactured by Japan Alcon K.K.).

The test drugs were suspended in a physiological saline. A 50 μl aliquot of 50 μl of the suspension (25 μg/eye of the test drug) was topically applied to one eye. The contralateral control eye received physiological saline. Intraocular pressure was measured at every 1 hr, until 6 hr, after topical application. In this experiment, 6 rabbits per group were used, and the mean values of intraocular pressure of the treated eye at each time were caluculated. The resuls are shown in FIG. 1.

Test drugs:

(1) 13,14-dihydro-15-keto-PGD$_2$; (○--------○)

(2) PGE$_2$; (●--------●)

As is obvious from the results, 13,14-dihydro-15-keto-PGs including 13,14-dihydro-15-keto-PGE$_2$ and the like are proved to possess ocular hypotensive potency without transient ocular hypertensive response that PGs including PGE$_2$ possess.

EXAMPLE 2

For the purpose of tonometry, Japanese White male rabbits (2.5-3.0 Kg) were fixed on braces. After topical anesthetization with 0.4% oxybuprocaine hydrochloride, intraocular pressure was measured using a pheumatic applanation tonometer (manufactured by Japan Alcon). After the topical application of 50 μl of the suspensions of the test drugs in a physiological saline to one eye, the intraocular pressure was measured and the intraocular pressure reduction (%) caused by each test drug was calculated. At the same time, the extent of conjunctival hyperemia was observed. The results are shown in Table 1.

TABLE 1

Table 1 (1)

| Test Drug | Dose (μg/eye) | Percent change of IOP | Hyperemia* |
|---|---|---|---|
| (1) | 100 | 22 | + |
| (2) | 100 | 26 | + |
| (3) | 100 | 24 | + |
| (4) | 100 | 30 | + |
| (5) | 100 | 31 | − |
| (6) | 100 | 33 | − |
| (7) | 50 | 23 | − |
| (8) | 50 | 27 | − |
| (9) | 100 | 40 | ++ |

Test drugs:
(1) 13,14-dihydro-15-keto-PGA$_1$ methyl ester
(2) 13,14-dihydro-15-keto-PGA$_1$ isopropyl ester
(3) 13,14-dihydro-15-keto-PGA$_2$ ethyl ester
(4) 13,14-dihydro-15-keto-PGA$_2$ isopropyl ester
(5) 13,14-dihydro-15-keto-20-ethyl-PGA$_1$ ethyl ester
(6) 13,14-dihydro-15-keto-20-ethyl-PGA$_1$ isopropyl ester
(7) 13,14-dihydro-15-keto-20-ethyl-PGA$_2$ methyl ester
(8) 13,14-dihydro-15-keto-20-ethyl-PGA$_2$ isopropyl ester
(9) PGA$_2$ Table 1 (2)

| Test Drug | Dose (μg/eye) | Percent change of IOP | Hyperemia* |
|---|---|---|---|
| (10) | 250 | 7 | + |
| (11) | 250 | 10 | + |
| (12) | 250 | 15 | + |
| (13) | 250 | 20 | + |
| (14) | 250 | 21 | − |
| (15) | 250 | 23 | − |
| (16) | 100 | 18 | − |
| (17) | 100 | 20 | − |
| (18) | 250 | 25 | ++ |

Test drugs:
(10) 13,14-dihydro-15-keto-PGB$_1$ methyl ester
(11) 13,14-dihydro-15-keto-PGB$_2$ isopropyl ester
(12) 13,14-dihydro-15-keto-PGB$_2$ methyl ester
(13) 13,14-dihydro-15-keto-PGB$_2$ isopropyl ester
(14) 13,14-dihydro-15-keto-20-ethyl-PGB$_1$ methyl ester
(15) 13,14-dihydro-15-keto-20-ethyl-PGB$_1$ isopropyl ester
(16) 13,14-dihydro-15-keto-20-ethyl-PGB$_2$ methyl ester
(17) 13,14-dihydro-15-keto-20-ethyl-PGB$_2$ isopropyl ester
(18) PGB$_2$ Table 1 (3)

| Test Drug | Dose (μg/eye) | Percent change of IOP | Hyperemia* |
|---|---|---|---|
| (19) | 250 | 8 | + |
| (20) | 250 | 11 | + |
| (21) | 250 | 18 | + |
| (22) | 250 | 20 | + |
| (23) | 250 | 20 | − |
| (24) | 250 | 22 | − |
| (25) | 100 | 21 | − |
| (26) | 100 | 25 | − |
| (27) | 250 | 23 | ++ |

Test drugs:
(19) 13,14-dihydro-15-keto-PGC$_1$ methyl ester
(20) 13,14-dihydro-15-keto-PGC$_1$ isopropyl ester
(21) 13,14-dihydro-15-keto-PGC$_2$ methyl ester
(22) 13,14-dihydro-15-keto-PGC$_2$ isopropyl ester
(23) 13,14-dihydro-15-keto-20-ethyl-PGC$_1$ methyl ester
(24) 13,14-dihydro-15-keto-20-ethyl-PGC$_1$ isopropyl ester
(25) 13,14-dihydro-15-keto-20-ethyl-PGC$_2$ methyl ester
(26) 13,14-dihydro-15-keto-20-ethyl-PGC$_2$ isopropyl ester
(27) PGC$_2$ Table 1 (4)

| Test Drug | Dose (μg/eye) | Percent change of IOP | Hyperemia* |
|---|---|---|---|
| (28) | 250 | 15 | ± |
| (29) | 250 | 17 | ± |
| (30) | 250 | 20 | ± |
| (31) | 250 | 18 | ± |
| (32) | 250 | 21 | ± |
| (33) | 250 | 25 | ± |
| (34) | 250 | 23 | ± |
| (35) | 100 | 13 | + |
| (36) | 250 | 28 | ± |
| (37) | 250 | 30 | ± |
| (38) | 250 | 24 | ± |
| (39) | 250 | 28 | ± |
| (40) | 250 | 31 | ± |
| (41) | 100 | 18 | ± |
| (42) | 100 | 20 | ± |
| (43) | 100 | 25 | ± |

Test drugs:
(28) 13,14-dihydro-15-keto-PGD$_1$ methyl ster
(29) 13,14-dihydro-15-keto-PGD$_1$ ethyl ester
(30) 13,14-dihydro-15-keto-PGD$_2$ ethyl ester
(31) 13,14-dihydro-15-keto-PGD$_2$ n-butyl ester
(32) 13,14-dihydro-15-keto-5,6-dehydro-PGD$_2$ methyl ester
(33) 13,14-dihydro-15-keto-5,6-dehydro-9β-PGD$_2$
(34) 13,14-dihydro-15-keto-5,6-dehydro-9β-PGD$_2$ methyl ester
(35) 13,14-dihydro-15-keto-16R,S-fluoro-PGD$_2$ methyl ester
(36) 13,14-dihydro-15-keto-16,16-dimethyl-PGD$_2$ methyl ester
(37) 13,14-dihydro-15-keto-19-methyl-PGD$_2$ methyl ester
(38) 13,14-dihydro-15-keto-20-methoxy-PGE$_2$
(39) 13,14-dihydro-15-keto-20-methoxy-PGE$_2$ n-butyl ester
(40) 13,14-dihydro-15-keto-16R,S-methyl-20-methoxy-PGD$_2$ methyl ester
(41) 13,14-dihydro-15-keto-20-ethyl-PGD$_1$ methyl ester
(42) 13,14-dihydro-15-keto-20-ethyl-PGD$_1$ ethyl ester
(43) 13,14-dihydro-15-keto-20-ethyl-PGD$_2$ methyl ester Table 1 (4) (continued)

| Test Drug | Dose (μg/eye) | Percent change of IOP | Hyperemia* |
|---|---|---|---|
| (44) | 100 | 23 | − |
| (45) | 100 | 20 | − |
| (46) | 250 | 28 | +++ |

Test drugs:
(44) 13,14-dihydro-15-keto-20-ethyl-PGD$_2$ ethyl ester
(45) 13,14-dihydro-15-keto-20-methoxyethyl-PGD$_2$ methyl ester
(46) PGD$_2$ Table 1 (5)

| Test Drug | Dose (μg/eye) | Percent change of IOP | Hyperemia* |
|---|---|---|---|
| (47) | 50 | 30 | + |
| (48) | 10 | 20 | + |
| (49) | 10 | 18 | + |
| (50) | 10 | 23 | + |
| (51) | 25 | 25 | ± |
| (52) | 25 | 32 | + |
| (53) | 25 | 18 | + |
| (54) | 25 | 20 | + |
| (55) | 25 | 23 | ± |
| (56) | 25 | 16 | + |
| (57) | 10 | 32 | + |
| (58) | 10 | 30 | + |
| (59) | 10 | 31 | + |
| (60) | 5 | 26 | + |
| (61) | 10 | 18 | + |
| (62) | 10 | 21 | + |

Test drugs:
(47) 13,14-dihydro-15-keto-PGE$_1$ ethyl ester
(48) 13,14-dihydro-6,15-diketo-PGE$_1$ ethyl ester
(49) 13,14-dihydro-6,15-diketo-PGE$_1$ n-butyl ester
(50) ±13,14-dihydro-6,15-diketo-PGE$_1$ ethyl ester
(51) 13,14-dihydro-6,15-diketo-11-dehydroxy-11R-methyl-PGE$_1$ ethyl ester
(52) 13,14-dihydro-6,15-diketo-16R,S-fluoro-11-dehydroxy-11R-methyl-PGE$_1$ ethyl ester
(53) 13,14-dihydro-6,15-diketo-16,16-dimethyl-PGE$_1$ ethyl ester
(54) 13,14-dihydro-6,15-diketo-19-methyl-PGE$_1$ methyl ester
(55) 13,14-dihydro-6,15-diketo-11-dehydroxy-11R-hydroxymethyl-PGE$_1$ methyl ester
(56) 13,14-dihydro-15-keto-PGE$_2$
(57) 13,14-dihydro-15-keto-PGE$_2$ methyl ester

TABLE 1-continued

(58) 13,14-dihydro-15-keto-PGE₂ isopropyl ester
(59) 13,14-dihydro-15-keto-Δ²-PGE₂ methyl ester
(60) 13,14-dihydro-15-keto-16R,S-fluoro-PGE₂ ethyl ester
(61) 13,14-dihydro-15-keto-3,16-dimethyl-PGE₂ methyl ester
(62) 13,14-dihydro-15-keto-16R,S-hydroxy-PGE₂ ethyl ester Table 1 (5) (continued)

| Test Drug | Dose (μg/eye) | Percent change of IOP | Hyperemia* |
|---|---|---|---|
| (63) | 10 | 25 | + |
| (64) | 25 | 21 | ± |
| (65) | 25 | 19 | ± |
| (66) | 25 | 23 | ± |
| (67) | 25 | 20 | — |
| (68) | 25 | 25 | — |
| (69) | 10 | 30 | — |
| (70) | 10 | 31 | — |
| (71) | 10 | 24 | — |
| (72) | 10 | 12 | — |
| (73) | 10 | 32 | +++** |

Test drugs:
(63) 13,14-dihydro-15-keto-19-methyl-PGE₂ ethyl ester
(64) 13,14-dihydro-15-keto-20-methoxy-PGE₂ methyl ester
(65) 13,14-dihydro-15-keto-20-methoxy-Δ²-PGE₂ methyl ester
(66) 13,14-dihydro-15-keto-16-dimethyl-20-methoxy-PGE₂ methyl ester
(67) 13,14-dihydro-15-keto-20-ethyl-PGE₁ methyl ester
(68) 13,14-dihydro-6,15-diketo-20-methyl-PGE₁ ethyl ester
(69) 13,14-dihydro-15-keto-20-ethyl-PGE₂ methyl ester
(70) 13,14-dihydro-15-keto-20-ethyl-PGE₂ ethyl ester
(71) 13,14-dihydro-15-keto-20-n-propyl-PGE₂ methyl ester
(72) 13,14-dihydro-15-keto-20-ethyl-11-dehydroxy-11R-methyl-PGE₂ methyl ester
(73) PGE₂

Table 1 (6)

| Test Drug | Dose (μg/eye) | Percent change of IOP | Hyperemia* |
|---|---|---|---|
| (74) | 100 | 28 | + |
| (75) | 100 | 22 | + |
| (76) | 100 | 33 | + |
| (77) | 100 | 38 | + |
| (78) | 20 | 25 | + |
| (79) | 10 | 42 | ± |
| (80) | 100 | 41 | + |
| (81) | 250 | 21 | + |
| (82) | 250 | 40 | + |
| (83) | 100 | 33 | ± |
| (84) | 25 | 17 | — |
| (85) | 50 | 28 | — |
| (86) | 50 | 28 | — |
| (87) | 50 | 25 | — |
| (88) | 50 | 23 | — |
| (89) | 250 | 23 | + |

Test drugs:
(74) 13,14-dihydro-15-keto-PGF₁α ethyl ester
(75) 13,14-dihydro-15-keto-PGF₂α methyl ester
(76) 13,14-dihydro-15-keto-PGF₂α ethyl ester
(77) 13,14-dihydro-15-keto-9β,11α-PGF₂ methyl ester
(78) 13,14-dihydro-15-keto-16R,S-fluoro-PGF₂α
(79) 13,14-dihydro-15-keto-16R,S-fluoro-PGF₂α methyl ester
(80) 13,14-dihydro-15-keto-16R,S-fluoro-11-dehydroxy-11R-methyl-PGF₂α methyl ester
(81) 13,14-dihydro-15-keto-16,16-dimethyl-PGF₂α ethyl ester
(82) 13,14-dihydro-15-keto-17S-methyl-PGF₂α ethyl ester
(83) 13,14-dihydro-15-keto-20-ethyl-PGF₁α methyl ester
(84) 13,14-dihydro-15-keto-20-ethyl PGF₂α
(85) 13,14-dihydro-15-keto-20-ethyl PGF₂α methyl ester
(86) 13,14-dihydro-15-keto-20-ethyl PGF₂α ethyl ester
(87) 13,14-dihydro-15-keto-20-ethyl PGF₂α isopropyl ester
(88) 13,14-dihydro-15-keto-20-ethyl PGF₂α n-butyl ester
(89) 13,14-dihydro-15-keto-20-methyl PGF₂α methyl ester Table 1 (6) (continued)

| Test Drug | Dose (μg/eye) | Percent change of IOP | Hyperemia* |
|---|---|---|---|
| (90) | 250 | 25 | ± |
| (91) | 250 | 26 | — |
| (92) | 25 | 43 | ± |
| (93) | 10 | 26 | ± |
| (94) | 250 | 30 | — |
| (95) | 250 | 18 | — |
| (96) | 100 | 46 | +++** |
| (97) | 25 | 27 | +++** |
| (98) | 25 | 31 | +++** |

**Lid closure and lacrimation were observed.
*The extent of conjunctival hyperemia:
—: scarcely observed
±: extremely weak hyperemia
+: slight hyperemia
++: pronounced hyperemia
+++: severe hyperemia Test drugs
(90) 13,14-dihydro-15-keto-20-n-propyl-PGF₂α methyl ester
(91) 13,14-dihydro-15-keto-20-n-butyl-PGF₂α methyl ester
(92) 13,14-dihydro-15-keto-20-ethyl-16R,S-fluoro-PGF₂α
(93) 13,14-dihydro-15-keto-20-ethyl-16R,S-fluoro-PGF₂α methyl ester
(94) 13,14-dihydro-15-keto-20-ethyl-11-dehydroxy-11R-methyl-PGF₂α methyl ester
(95) 13,14-dihydro-15-keto-20-ethyl-16R,S-fluoro-11-dehydroxy-11R-methyl-PGF₂α methyl ester
(96) PGF₂α
(97) PGF₂α methyl ester
(98) PGF₂α isopropyl ester The n.m.r. of the above compounds used in the Example 2 and Mass are shown hereinafter:
¹H n.m.r was determined using heavy chloroform as a solvent by a NMR spectrometer R-90H available from Hitachi Seisakusho.
Mass was determined by a mass spectrometer M-80B available from Hitachi Seisaku-sho;
EI method: at ionization patential of 70 eV, SIMS method: silver plate-glycerin matrix Compound (3)
δ: 0.88(3H, t, J=6Hz), 1.25(3H, t, J=7Hz), 1.10–2.75(22H, m), 4.11(2H, q, J=7Hz), 5.37(2H, m), 6.12(1H, dd, J=6Hz, J=2.5Hz), 7.53(1H, dd, J=6Hz, J=3Hz)

Compound (8)
δ: 0.86(3H, t, J=5.5Hz), 1.21(6H, d, J=6Hz), 1.05–2.75(26H, m), 4.96(1H, hept, J=6Hz), 5.37(2H, m), 6.09(1H, dd, J=6Hz, J=2Hz), 7.50(1H, J=6Hz, J=2.5Hz)
Mass(EI) m/z 404(M⁺), 345(M⁺−i-C₃H₇O)

Compound (30)
δ: 0.89(3H, t, J=6Hz), 1.26(3H, t, J=7Hz), 1.06–2.93(25H, m), 4.13(2H, q, J=7Hz), 4.41(1H, m), 5.47(2H, m)

Compound (34)
δ: 0.89(3H, t, J=6Hz), 1.09–2.96(25H, m), 3.63(3H, s), 4.19(1H, m)

Compound (35)
δ: 0.91(3H, t, J=6Hz), 1.1–2.93(23H, m), 3.64(3H, s), 4.3–4.5(1.5H, m), 4.98(0.5H, dd, J=6Hz), 5.50(2H, m)
Mass(SIMS) m/z 385(M+H)⁺, 367(M⁺+1−H₂O), 365(M⁺+1−HF)

Compound (37)
δ: 0.86(6H, d, J=7Hz), 0.94–2.90(24H, m), 3.64(3H, s), 4.38(1H, m), 5.43(2H, m)
Mass(EI) m/z 380(M⁺), 362(M⁺−H₂O), 331, 234, 222

Compound (40)
δ: 1.05(3H, d, J=7Hz), 0.80–2.83(24H, m), 3.28(3H, s), 3.32(2H, t, J=6Hz), 3.64(3H, s), 4.29–4.47(1H, m), 5.44(2H, m)

Compound (45)
δ: 1.10–2.95(29H, m), 3.30(3H, s), 3.33(2H, t, J=6Hz), 3.66(3H, s), 4.38(1H, m), 5.44(2H, m)

Compound (55)
δ: 0.86(6H, d, J=6Hz), 0.98–2.98(26H, m), 2.71(1H, m), 3.63(3H, s), 3.50–3.81(2H, m)
Mass(EI) m/z 410(M⁺), 392(M⁺−18), 379, 361

Compound (58)
δ: 0.88(3H, t, J=6Hz), 1.22(6H, d, J=6.5Hz), 1.07–3.03(25H, m), 4.03(1H, m), 4.97(1H, hept, J=6.5Hz), 5.37(2H, m)

Compound (67)
δ: 0.87(3H, t, J=6Hz), 1.03–2.84(33H, m), 3.64(3H, s), 3.98(1H, m)

Compound (68)
δ: 0.87(3H, t, J=6Hz), 1.23(3H, t, J=7Hz), 1.03–2.88(29H, m), 4.08(2H, q, J=7Hz), 3.86–4.23 (1H m)

Compound (69)

TABLE 1-continued

δ: 0.88(3H, t, J=6Hz), 1.07-2.90(29H, m), 3.64(3H, s), 4.02(1H, m), 5.35(2H, m)
Compound (70)
δ: 0.87(3H, t, J=6Hz), 1.23(3H, t, J=7Hz), 1.07-2.83(29H, m), 4.08(2H, q, J=7Hz), 3.79-4.22(1H, m), 5.34(2H, m)
Mass(EI) m/z 408,390,345
Compound (71)
δ: 0.87(3H, t, J=5Hz), 1.00-2.83(31H, m), 3.63(3H, s), 3.86-4.15(1H, m), 5.34(2H, m)
Mass(SIMS) m/z 409,391,369
Compound (72)
δ: 0.87(3H, t, J=5Hz), 1.11(3H, d, J=6Hz), 1.00-2.60(29H, m), 3.63(3H, s), 5.33(2H, m)
Mass(EI) m/z 392,374,361,343
Compound (83)
δ: 0.87(3H, t, J=6Hz), 1.15-2.70(34H, m), 3.63(3H, s), 3.86(1H, m), 4.15(1H, m)
Mass(EI) m/z 398($M^+$),380($M^+$ $-$ 18),362,349
Compound (84)
δ: 0.86(3H, t, J=6Hz), 1.15-2.70(28H, m), 3.85(1H, m), 4.12(1H, m), 5.10-5.75(5H, m)
Mass(EI) m/z 364($M^+$ $-$ 18), 346
Compound (85)
δ: 0.87(3H, t, J=6Hz), 1.10-2.65(30H, m), 3.63(3H, s), 3.85(1H, m), 4.13(1H, m), 5.38(2H, m)
Mass(SIMS) m/z 397($M^+$ +1), 379($M^+$ +1$-H_2O$), 361($M^+$ +1$-2H_2O$), 345,330
Compound (86)
δ: 0.87(3H, t, J=6Hz), 1.24(3H, t, J=7Hz), 1.10-2.95(30H, m), 3.85(1H, m), 4.08(2H, q, J=7Hz), 3.93-4.25(1H, m), 5.38(2H, m)
Mass(EI) m/z 410($M^+$),392($M^+$ $-$ 18),374
Compound (87)
δ: 0.87(3H, t, J=6Hz), 1.22(6H, d, J=6.5Hz), 1.10-2.75(30H, m), 3.85(1H, m), 4.13(1H, m), 4.95(1H, hept, J=6.5Hz), 5.38(2H, m)
Mass(EI) m/z 424($M^+$),406($M^+$ $-$ 18),388,347
Compound (88)
δ: 0.70-1.03(6H, m), 1.10-3.05(34H, m), 3.84(1H, m), 4.03(2H, t, J=6.5Hz), 4.10(1H, m), 5.38(2H, m)
Mass(EI) m/z 420($M^+$),402($M^+$ $-$ 18),376,347
Compound (89)
δ: 0.87(3H, t, J=6Hz), 1.15-2.70(28H, m), 3.62(3H, s), 3.83(1H, m), 4.12(1H, m), 5.37(2H, m)
Mass(SIMS) m/z 383($M^+$ +1), 365($M^+$ +1$-$18), 347
Compound (90)
δ: 0.87(3H, t, J=6Hz), 1.10-2.70(32H, m), 3.63(3H, s), 3.85(1H, m), 4.12(1H, m), 5.38(2H, m)
Compound (91)
δ: 0.87(3H, t, J=6Hz), 1.10-2.70(34H, m), 3.63(3H, s), 3.83(1H, m), 4.12(1H, m), 5.38(2H, m)
Compound (92)
δ: 0.87(3H, t, J=6Hz), 1.10-2.90 (26H, m), 3.87(1H, m), 4.12(1H, m), 4.43(0.5H, m), 4.50-5.10(3H, brs),4.99(0.5H, m), 5.38(2H, m)
Mass(EI) m/z 400($M^+$), 382($M^+$), 382($M^+$ $-$ 18,362,344
Compound (94)
δ: 0.87(3H, t, J=5.5Hz), 1.06(3H, d, J=6Hz), 1.15-2.55(30H, m), 3.63(3H, s), 4.08(1H, m), 5.38(2H, m)
Mass(EI) m/z 394($M^+$), 375($M^+$ $-$ 18), 358,344
Compound (95)
δ: 0.88(3H, t, J=6Hz), 1.08(3H, d, J=6Hz), 1.15-2.75(28H, m), 3.63(3H, s), 4.09(1H, m), 4.42(0.5H, m), 4.97(0.5H, m), 5.38(2H, m)
Mass(EI) m/z 412($m^+$), 394($M^+$ $-$ 18)

EXAMPLE 3

For the purpose of tonometry, Japanes White male rabbits (2.5 Kg-3.0 Kg) were fixed on braces. After anesthetization by topical application of 0.4 % oxybuprocaine hydrochloride, the intraocular pressure was determined using a pheumatic applanation tonometer (manufactured by Japan Alcon K.K.).

The test drugs were suspended in a physiological saline, and a 50 μl aliquot (25 μg/eye of the test drug) was topically applied to one eye, while the other eye received physiological saline. At every 0.5 hr after topical application, up to 2 hr, the intraocular pressure was measured and side effects were observed and assessed. In this experiment, 6 rabbits per group were used, and mean value of the intraocular pressure of the treated eye (the change (mmHg) provided that the intraocular pressure at 0 hr is 0) and rating of the assessment of the side effects at each time were determined. The side effects were rated according to the following standard.

The results are shown in Tables 2 and 3.

TABLE 2

(Charge in intraocular pressure; Means ± S.E. mmHg)

| Test Drug | Time (hr) | | | |
|---|---|---|---|---|
| | 0.5 | 1.0 | 1.5 | 2.0 |
| 1 | −1.7 ± 0.5 | −3.5 ± 1.0 | −2.5 ± 1.4 | −1.2 ± 1.8 |
| 4 | +4.0 ± 1.1 | +0.8 ± 1.4 | +0.5 ± 1.0 | −0.5 ± 1.9 |
| 2 | −2.9 ± 0.7 | −5.4 ± 1.5 | −6.4 ± 1.1 | −6.3 ± 1.1 |
| 5 | +5.3 ± 0.8 | +10.3 ± 0.4 | +5.4 ± 1.4 | +0.2 ± 1.4 |
| 3 | −2.3 ± 1.0 | −4.3 ± 1.9 | −4.8 ± 1.1 | −4.8 ± 0.7 |
| 6 | +2.2 ± 1.1 | +3.8 ± 2.5 | +1.5 ± 1.9 | −1.0 ± 1.8 |

TABLE 3

(Evaluation of side effects)

| Test Drug | Time (hr) | | | |
|---|---|---|---|---|
| | 0.5 | 1.0 | 1.5 | 2.0 |
| 1 | 2.2 ± 0.2 | 2.0 ± 0.3 | 1.5 ± 0.2 | 1.2 ± 0.4 |
| 4 | 3.2 ± 0.4 | 3.0 ± 0.6 | 2.8 ± 0.5 | 2.5 ± 0.3 |
| 2 | 2.8 ± 0.3 | 3.1 ± 0.3 | 2.7 ± 0.4 | 2.2 ± 0.5 |
| 5 | 5.0 ± 0.0 | 5.2 0.2 | 5.0 ± 0.0 | 4.8 ± 0.2 |
| 3 | 2.0 ± 0.4 | 2.3 ± 0.6 | 2.0 ± 0.5 | 1.7 ± 0.7 |
| 6 | 5.0 ± 0.0 | 5.2 ± 0.2 | 5.3 ± 0.2 | 5.3 ± 0.3 |

Standard of the evaluation of the side effects (ocular response)

Scale for Scoring Ocular Lesions

1) Cornea
A) Opacity-degree of density (area most dense taken for reading)

| | |
|---|---|
| No Opacity | 0 |
| Scattered or diffuse area, details of iris clearly visible | 1 |
| Easily discernible translucent areas, details of iris slightly obscured | 2 |
| Opalescent areas, no details of iris visible, size of pupil barely discernible | 3 |
| Opaque, iris invisible | 4 |

B) Area of cornea involved

| | |
|---|---|
| One quarter (or less) but not zero | 1 |
| Greater than one quarter, but less than half | 2 |
| Greater than half, but less than three quarters | 3 |
| Greater than three quarters, up to whole area | 4 |

A × B × 5    Total maximum = 80

2) Iris
A) Values

| | |
|---|---|
| Normal | 0 |
| Folds above normal, congestion, swelling, circumcorneal injection (any or all of these or combination of any thereof) iris still reacting to light (sluggish reaction is positive) | 1 |
| No reaction to light, hemorrhage, gross destruction (any or all of these) | 2 |

A × 5    Total maximum = 10

3) Conjunctivae
A) Redness (refers to palpebral and bulbar conjunctivae excluding cornea and iris)

| | |
|---|---|
| Vessels normal | 0 |
| Vessels definitely injected above normal | 1 |
| More diffuse, deeper crimson red, individual vessels not easily discernible | 2 |
| Diffuse beefy red | 3 |

B) Chemosis

| | |
|---|---|
| No swelling | 0 |
| Any swelling above normal (includes | 1 |

TABLE 3-continued

| | |
|---|---|
| nictitating membrane) | |
| Obvious swelling with partial eversion of lids | 2 |
| Swelling with lids about half closed | 3 |
| Swelling with lids about half closed to completely closed | 4 |
| C) Discharge | |
| No discharge | 0 |
| Any amount different from normal (dose not include small amounts observed in inner canthus of normal animals) | 1 |
| Discharge with moistening of the lids and hairs just adjacent to lids | 2 |
| Discharge with moistening of the lids and hairs, and considerable area around the eye | 3 |
| Score (A' + B + C) × 2 Total maximum = 20 | |

Test Drugs:
1. 13,14-dihydro-15-keto-20-ethyl-PGF$_2\alpha$
2. 13,14-dihydro-15-keto-20-ethyl-PGF$_2\alpha$ methyl ester
3. 13,14-dihydro-15-keto-20-ethyl-PGF$_2\alpha$ isopropyl ester
4. PGF$_2\alpha$
5. PGF$_2\alpha$ methyl ester
6. PGF$_2\alpha$ isopropyl ester As is obvious from above resluts, 13,14-dihydro-15-keto-20-alkyl-PGs including 13,14-dihydro-15-keto-20-ethyl-PGF$_2$s cause intraocular pressure reduction without transient ocular hypertensive response connected with PGs including PGF$_2$s. Esters are proved to have a stronger tendency to cause intraocular pressure reduction than carboxyl acid type. Compared with PGs including PGF$_2$s, 13,14-dihydro-15-keto-20-alkyl-PGs including 13,14-dihydro-15-keto-20-ethyl-PGF$_2$s are accompanied with extremely reduced side effects, which are hardly detectable.

EXAMPLE 4

For the purpose of tonometry, Japanese White male rabbits (2.5 Kg–3.0 Kg) were fixed on braces. After anesthetization by topical application of 0.4 % oxybuprocaine hydrochloride, the intraocular pressure was determined using on a pheumatic applanation tonometer (manufactured by Japan Alcon K.K.).

The test drugs were suspended in a physiological saline, and a 50 μl aliquot (25 μg/eye of the test drug) was topically applied to one eye, while the other eye received physiological saline. At every 1 hr after topical application, up to 4 hr, the intraocular pressure was measured.

The results are shown in Table 4

TABLE 4

| Test Drug | Time | | | | |
|---|---|---|---|---|---|
| | 0 | 1 | 2 | 3 | 4 |
| 1 | 21.3 ± 3.6[1)] | 29.3 ± 3.5 | 22.0 ± 3.4 | 19.8 ± 1.5 | 18.5 ± 1.9 |
| | | (+37.6)[2)] | (+3.3) | (−7.0) | (−13.1) |
| 2 | 17.7 ± 1.5 | 14.3 ± 1.5 | 12.7 ± 3.2 | 12.3 ± 2.9 | 14.3 ± 3.8 |
| | | (−19.2) | (−28.2) | (−30.5) | (−19.2) |

Test Drugs:
1. PGE$_2$
2. 13,14-dihydro-15-keto-20-ethyl-PGE$_2$ isopropyl ester

[1)]: Mean ± S.E. of intraocular pressure (mmHg)
[2)]: Percent change of intraocular pressure (%)

We claim:

1. A topical ocular composition comprising an amount effective as an ocular hypotensive agent of a 13,14-dihydro-15-keto-prostaglandin represented by the following formula (I):

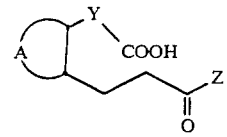

wherein A is

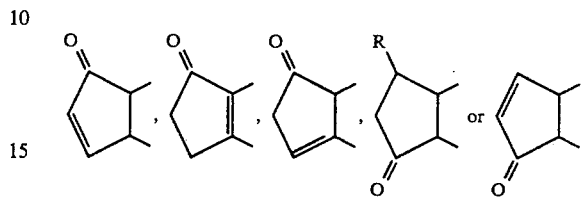

wherein R is hydroxy, hydroxy $C_{1-3}$ alkyl or $C_{1-2}$ alkyl; Y is a saturated or unsaturated $C_{2-6}$ hydrocarbon chain which is unsubstituted or substituted by oxo, halogen, an alkyl group or hydroxyl; Z is a $C_{1-10}$ saturated or unsaturated hydrocarbon forming a straight-chain, a branched-chain or a ring, which is unsubstituted or substituted by halogen, an alkyl group, an alkoxy group, hydroxyl, a phenyl group or a phenoxy group; or the physiologically acceptable salts and carboxylic acid esters of the compounds of formula (I) said ester being a straight or branched-chain alkyl containing up to one unsaturated bond, cycloalkyl, benzyl, phenyl, hydroxyalkyl, alkoxyalkyl, alkylsilyl or tetrahydropyranyl ester, of a compound of Formula (I); and a pharmaceutically acceptable carrier.

2. A method for treating ocular hypertension in a human patient needing such treating which comprises administering to said patient an amount of a 13,14-dihydro-15-keto-prostaglandin of the formula (I) effective to treat ocular hypertension

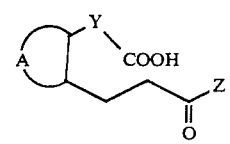

wherein A is

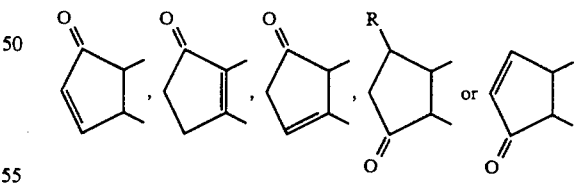

wherein R is hydroxy, hydroxy $C_{1-3}$ alkyl or $C_{1-2}$ alkyl; Y is a saturated or unsaturated $C_{2-6}$ hydrocarbon chain which is unsubstituted or substituted by oxo, halogen, an alkyl group or hydroxyl; Z is a $C_{1-10}$ saturated or unsaturated hydrocarbon forming a straight-chain, a branched-chain or a ring, which is unsubstituted or substituted by halogen, an alkyl group, an alkoxy group, hydroxyl, a phenyl group or a phenoxy group; or the physiologically acceptable salts and carboxylic acid esters of the compounds of formula (I) said ester being a straight or branched-chain alkyl containing up to one unsaturated bond, cycloalkyl, benzyl, phenyl, hydroxyalkyl, alkoxyalkyl, alkylsilyl or tetrahydropyranyl ester, of a compound of Formula (I).

3. A method for treating glaucoma in a human patient needing such treatment which comprises administering to said patient an amount of a 13,14-dihydro-15-keto-prostaglandin of the following formula (I) effective to treat glaucoma

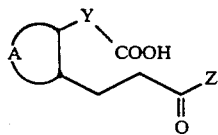

wherein A is

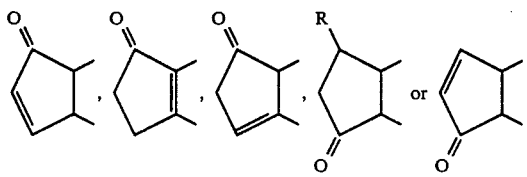

wherein R is hydroxy, hydroxy $C_{1-3}$ alkyl of $C_{1-2}$ alkyl; Y is a saturated or unsaturated $C_{2-6}$ hydrocarbon chain which is unsubstituted or substituted by oxo, halogen, an alkyl group or hydroxyl; Z is a $C_{1-10}$ saturated or unsaturated hydrocarbon forming a straight-chain, a branched-chain or a ring, which is unsubstituted or substituted by halogen, an alkyl group, an alkoxy group, hydroxyl, a phenyl group or a phenoxy group; or the physiologically acceptable salts and carboxylic acid esters of the compounds of formula (I) said ester being a straight or branched-chain alkyl containing up to one unsaturated bond, cycloalkyl, benzyl, phenyl, hydroxyalkyl, alkoxyalkyl, alkylsilyl or tetrahydropyranyl ester, a the compound of Formula (I).

4. The method of claim 2, wherein the carboxyl group at the end of the α-chain in the 13,14-dihydro-15-keto-prostaglandin is in the form of an alkyl ester.

5. The method of claim 2, wherein the 13,14-dihydro-15-keto-prostaglandin is in the form of a 20-alkyl having an alkyl group at the C-20 position.

6. The method of claim 2, wherein the 13,14-dihydro-15-keto-prostaglandin is a prostaglandin of the A series.

7. The method of claim 2, wherein the 13,14-dihydro-15-keto-prostaglandin is a prostaglandin of the B series.

8. The method of claim 2, wherein the 13,14-dihydro-15-keto-prostaglandin is a prostaglandin of the C series.

9. The method of claim 2, wherein the 13,14-dihydro-15-keto-prostaglandin is a prostaglandin of the D series.

10. The method of claim 2, wherein the 13,14-dihydro-15-keto-prostaglandin is a prostaglandin of the J series.

11. The method of any of claims 2 or 4–10, wherein said administration s topically to the eye.

12. The method of claim 3, wherein the carboxyl group at the end of the α-chain in the 13,14-dihydro-15-keto-prostaglandin is in the form of an alkyl ester.

13. The method of claim 3, wherein the 13,14-dihydro-15-keto-prostaglandin is in the form of a 20-alkyl having an alkyl group at the C-20 position.

14. The method of claim 3, wherein the 13,14-dihydro-15-keto-prostaglandin is a prostaglandin of the A series.

15. The method of claim 3, wherein the 13,14-dihydro-15-keto-prostaglandin is a prostaglandin of the B series.

16. The method of claim 3, wherein the 13,14-dihydro-15-keto-prostaglandin is a prostaglandin of the C series.

17. The method of claim 3, wherein the 13,14-dihydro-15-keto-prostaglandin is a prostaglandin of the D series.

18. The method of claim 3, wherein the 13,14-dihydro-15-keto-prostaglandin is a prostaglandin of the J series.

19. The method of any of claims 4 or 12–19, wherein said administration is topically to the eye.

20. The ocular hypotensive composition according to claim 1, wherein the carboxyl group at the end of the α-chain in the 13,14-dihydro-15-keto-prostaglandin is in the form of an alkyl ester.

21. The ocular hypotensive compositions according to claim 1, wherein the 13,14-dihydro-15-keto-prostaglandin is in the form of 20-alkyl having an alkyl group at the C-20 position.

22. The ocular hypotensive compositions according to claim 1, wherein the 13,14-dihydro-15-keto-prostaglandin is a prostaglandin of the A series.

23. The ocular hypotensive compositions according to claim 1, wherein the 13,14-dihydro-15-keto-prostaglandin is a prostaglandin of the B series.

24. The ocular hypotensive compositions according to claim 1, wherein the 13,14-dihydro-15-keto-prostaglandin is a prostaglandin of the C series.

25. The ocular hypotensive compositions according to claim 1, wherein the 13,14-dihydro-15-keto-prostaglandin is a prostaglandin of the D series.

26. The ocular hypotensive compositions according to claim 1, wherein the 13,14-dihydro-15-keto-prostaglandin is a prostaglandin of the J series.

* * * * *